(12) United States Patent
Ichikawa et al.

(10) Patent No.: US 9,489,917 B2
(45) Date of Patent: Nov. 8, 2016

(54) COLOR PERCEPTION TESTER, CONTROL PROGRAM AND METHOD OF CONTROLLING COLOR PERCEPTION TESTER

(75) Inventors: Kazuo Ichikawa, Aichi-ken (JP); Kiyoshi Tanaka, Nagano-ken (JP); Yoshiki Tanaka, Nagano-ken (JP); Takuya Hara, Shizuoka-ken (JP)

(73) Assignees: Ichikawa Kazuo, Nagoya-Shi, Achi (JP); Shinshu University, Matsumoto (JP); Kowa Company, Ltd., Aichi-Ken (JP)

( * ) Notice: Subject to any disclaimer, the term of this patent is extended or adjusted under 35 U.S.C. 154(b) by 619 days.

(21) Appl. No.: 13/641,177

(22) PCT Filed: Apr. 12, 2011

(86) PCT No.: PCT/JP2011/059072
§ 371 (c)(1),
(2), (4) Date: Nov. 29, 2012

(87) PCT Pub. No.: WO2011/129324
PCT Pub. Date: Oct. 20, 2011

(65) Prior Publication Data
US 2013/0069973 A1    Mar. 21, 2013

(30) Foreign Application Priority Data
Apr. 14, 2010    (JP) .................................. 2010-092872

(51) Int. Cl.
G09G 5/02    (2006.01)
G06T 11/00    (2006.01)
A61B 3/032    (2006.01)
A61B 3/06    (2006.01)

(52) U.S. Cl.
CPC ................. *G09G 5/02* (2013.01); *A61B 3/032* (2013.01); *A61B 3/066* (2013.01); *G06T 11/00* (2013.01)

(58) Field of Classification Search
CPC ............ A61B 3/02–3/09; G06T 11/00–11/80; G09G 5/02–5/06
See application file for complete search history.

(56) References Cited

U.S. PATENT DOCUMENTS 4,349,250 A * 9/1982 Gelius .......................... 351/239
5,347,622 A * 9/1994 Takemoto et al. ............ 345/629

(Continued)

FOREIGN PATENT DOCUMENTS

JP    2813522 B2    8/1998
JP    2004 321659 A    11/2004

(Continued)

*Primary Examiner* — Charles Tseng
(74) *Attorney, Agent, or Firm* — Law Offices of Robert F. Zielinski LLC (57) ABSTRACT

A color perception test has a color matching processor that executes a color matching processing on a color monitor, and an image display controller that displays two or more images for color perception test in order on the color monitor on which the color matching processing was done. When displaying each image for color perception test, a color perception test is done in a state that one of its hue, brightness, saturation and display time is changed and the other elements are fixed. Since the color perception tester has the color matching processor, colors of the image are not changed with passage of time different from color printed one, and correct test can be done thereby. If the test is periodically done on some examinee, a degree of decreasing color perception function by aging can be exactly known.

21 Claims, 3 Drawing Sheets

(56) References Cited

U.S. PATENT DOCUMENTS

| | | | | |
|---|---|---|---|---|
| 5,353,391 A | * | 10/1994 | Cohen et al. | 345/619 |
| 5,463,725 A | * | 10/1995 | Henckel et al. | 715/776 |
| 5,694,199 A | * | 12/1997 | Rodriguez | 351/223 |
| 6,227,668 B1 | * | 5/2001 | McKinnon et al. | 351/222 |
| 6,350,032 B1 | * | 2/2002 | Menozzi et al. | 351/239 |
| 6,486,900 B1 | * | 11/2002 | Shen et al. | 715/867 |
| 6,623,119 B2 | * | 9/2003 | Lehmeier et al. | 351/239 |
| 6,956,580 B2 | * | 10/2005 | Rozzi | 345/589 |
| 7,993,003 B2 | * | 8/2011 | Carda et al. | 351/242 |
| 2004/0046934 A1 | * | 3/2004 | Sponsel et al. | 351/200 |
| 2007/0121066 A1 | * | 5/2007 | Nashner | 351/210 |

FOREIGN PATENT DOCUMENTS

| | | |
|---|---|---|
| JP | 2006 130304 A | 5/2006 |
| JP | 2007 75339 A | 3/2007 |
| JP | 3974704 B2 | 6/2007 |
| JP | 3984996 B2 | 7/2007 |
| JP | 2008 165083 A | 7/2008 |
| JP | 2008 268376 A | 10/2008 |

* cited by examiner

COLOR PERCEPTION TESTER, CONTROL PROGRAM AND METHOD OF CONTROLLING COLOR PERCEPTION TESTER

CROSS-REFERENCE TO RELATED PATENT APPLICATIONS

The present application is a U.S. national stage application under 35 U.S.C. §371 of PCT Application No. PCT/JP2011/059072 filed Apr. 12, 2011, which in turn claims the benefit of priority of Japanese Patent Application No. 2010-092872, filed Apr. 14, 2010, the entireties of which are incorporated herein by reference.

TECHNICAL FIELD

The invention relates to a color perception tester for successively displaying two or more images for color perception test on a color monitor, a control program and a method of controlling the color perception tester.

BACKGROUND ART

A conventional color perception test is conducted in such a manner that an examiner presents a color perception test plate that is printed on a book or a card in colors, such as ISHIHARA color blind test plate, to an examinee, and whether or not the examinee can perceive a stimulus in the plate, such as a character, a number, Landolt ring and the other figures, is searched (see non-patent related document 1)

PRIOR ART

Non-Patent Related Document

[Non-Patent related document 1]:
   International version of ISHIHARA Color blind test plate 38

Problems to be Solved by Invention

A color perception function decreases by aging and in some cases, people whishes to know a degree of decreasing. But, it may be not possible to test the degree of decreasing the color perception function even if a reexamination is conducted on some examinee with the same color perception test plate since the color perception test plate printed on a book or a card in colors may be changed in its colors with passage of time. And, the color perception test has such a characteristic that even if they do not perceive the stimulus at a moment to see it, eyes are getting used to see the stimulus and can perceive the stimulus after passage of two or three seconds since the color perception test closely depends on the presentation time of the stimulus. If the above-mentioned book or card is used, it is not possible to control the presentation time of the stimulus and the presentation time widely varies, and it is not possible to correctly test.

An object of the invention is to provide a color perception tester, a control program and a method of controlling color perception tester for solving such problems.

Means for Solving Problems

The invention according to claim 1 relates to a color perception tester (1), comprising:

a color matching processor (3) that executes a color matching processing on a color monitor (2);

an image display controller (4) that executes at least one display step wherein two or more images for color perception test are displayed in order on said color monitor (2) on which said color matching processing was done;

whereby said image display controller (4) changes a first element, one element of six elements, hue, brightness, saturation and display time of each image for color perception test and brightness of a background or a stimulus if said image for color perception test is comprised of said background image and said stimulus shown in said background image and fixes said five elements excluding said first element when displaying said two or more images for color perception test in said one display step.

The invention according to claim 2 relates to the color perception tester according to claim 1, wherein said image display controller (4) executes at least two display steps, a first display step (S1 of FIG. 2) wherein two or more images for color perception test are displayed in order on said color monitor (2) on which said color matching processing was done, and a second display step (S2 of FIG. 2) wherein two or more images for color perception test are displayed in order on said color monitor (2), and said image display controller (4) changes said first element when displaying each image for color perception test in each display step, and gradually changes said second element that is one element excluding said first element in said first display step (S1) and said second display step (S2), and fixes said four elements excluding said first element and said second element in said first display step (S1) and said second display step (S2).

The invention according to claim 3 relates to the color perception tester according to claim 1 or 2, wherein said image display controller (4) has a display time controller (5) that controls display time of each image for color perception test.

The invention according to claim 4 relates to the color perception tester according to claims 1 to 3, further comprising a test result display (6) that displays a kind of displayed image for color perception test, information on color combination used in displayed image for color perception test, a result whether or not an examinee can perceive said image for color perception test and display time of said image for color perception test.

The invention according to claim 5 relates to the color perception tester according to claims 1 to 4, further comprising an image data storage (7) that stores two or more images for color perception test, wherein said image display controller (4) displays said image for color perception test stored in said image data storage (7).

The invention according to claim 6 relates to the color perception tester according to claims 1 to 4, further comprising an image composer (8) that composes said image for color perception test to be displayed, wherein said image display controller (4) displays said image for color perception test that was composed through said image composer (8).

The invention according to claim 7 relates to the color perception tester according to claim 6, further comprising an image data storage (7) that stores two or more images for color perception test, wherein said image for color perception test composed through said image composer (8) is temporally stored in said image data storage (7).

The invention according to claim 8 relates to the color perception tester according to claims 1 to 7, wherein said image display controller (4) displays an image in gray color on said color monitor (2) for a predetermined time during switching said image for color perception test.

The invention according to claim 9 relates to the color perception tester according to claims 1 to 8, further comprising a statistical data computer (not shown) that computes test results of a color perception test done on an examinee group as statistical data, an accumulated data storage (not shown) that stores two or more statistical data obtained from said examinee group as accumulated data, and a data comparator (not shown) that compares said test result of said color perception test done on some examinee with said accumulated data.

The invention according to claim 10 relates to control program for controlling a computer (C of FIG. 1), for getting said computer (C) to function as the followings:
  a color matching processor (3) that executes a color matching processing on a color monitor (2);
  an image display controller (4) that executes at least one display step wherein two or more images for color perception test are displayed in order on said color monitor (2) on which said color matching processing was done;
  whereby said image display controller (4) changes a first element, one of six elements, hue, brightness, saturation and display time of each image for color perception test and brightness of a background or a stimulus if said image for color perception test is comprised of said background and said stimulus shown in said background image and fixes five elements excluding said first element when displaying two or more images for color perception test in said one display step.

The invention according to claim 11 relates to the control program according to claim 10, wherein said image display controller (4) executes at least two display steps, a first step (S1) wherein two or more images for color perception test are displayed in order on said color monitor (2) on which said color matching processing was done, and a second display step (S2) wherein two or more images for color perception test are displayed in order on said color monitor (2); and said image display controller (4) changes said first element when displaying each image for color perception test in each display step, and gradually changes said second element that is one element excluding said first element in said first display step (S1) and said second display step (S2), and fixes said four elements excluding said first element and said second element in said first display step (S1) and said second display step (S2).

The invention according to claim 12 relates to the control program according to claim 10 or 11, for getting a computer to function as followings:
  a statistical data computer (not shown) that computes test result of a color perception test done on said examinee group as statistical data,
  an accumulated data storage (not shown) that stores two or more statistical data obtained from said examinee group as accumulated data; and
  a data comparator (not shown) that computes said test result of said color perception test done on some examinee with said accumulated data.

The invention according to claim 13 relates to a method of controlling a color perception tester, comprising:
  a step of executing a color matching processing on a color monitor (2) through a color matching processor (3);
  a step of executing at least one display step wherein two or more images for color perception test are displayed in order on said color monitor (2) on which said color matching processing was done through said image display controller (4);
  whereby said image display controller (4) changes a first element, one first element of six elements, hue, brightness, saturation and display time of each image for color perception test and brightness of a background or a stimulus if said image for color perception test is comprised of said background image and said stimulus shown in said background image and fixes said five elements excluding said first element when displaying two or more images for color perception test in said one display step.

The invention according to claim 14 relates to the method of controlling the color perception tester according to claim 13, wherein said image display controller (4) executes at least two display steps, a first display step (S1) wherein two or more images for color perception test are displayed in order on said color monitor (2) on which said color matching processing was done, and a second display step (S2) wherein two or more images for color perception test are displayed in order on said color monitor (2), and said image display controller (4) changes said first element when displaying each image for color perception test in each display step, and gradually changes said second element that is one element excluding said first element in said first display step (S1) and said second display step (S2), and fixes said four elements excluding said first element and said second element in said first display step (S1) and said second display step (S2).

The invention according to claim 15 relates to the method of controlling the color perception tester according to claim 13 or 14, further comprising:
  a step of computing test result of a color perception test done on said examinee group as statistical data through a statistical data computer (not shown),
  a step of storing two or more statistical data obtained from said examinee group as accumulated data through an accumulated data storage (not shown); and
  a step of comparing said test result of said color perception test done on some examinee with said accumulated data through a data comparator (not shown).

The number in parentheses shows the corresponding element in the drawings for the sake of convenience, accordingly, the descriptions are not restricted and bound by the descriptions on the drawings.

Effects of Invention

According to the inventions according to claims 1, 4, 5, 6, 7, 10 and 13, the image for color perception test is not changed with passage of time different from one printed on a book or a card since the color matching processor executes the color matching processing on the color monitor, and its color quality can be maintained and correct color test can be done. Even if the test is done on some examinee again, it is possible to exactly know a degree of decreasing color perception function by aging since the color quality of the image for color perception test is not changed with passage of time.

According to the invention according to claim 3, it is possible to improve credibility on the test results by preventing the display time of each image for color perception test from widely varying.

According to the inventions according to claims 9, 12 and 15, it is possible to compare the test result of the color perception test of some examinee with the accumulated data of the examinee group and to obtain statistical evaluation of the color perception function of the new examinee (in other words, relative evaluation when comparing with the examinee group).

According to the inventions according to claims 2, 11 and 14, it is possible to obtain more detailed test results by comparing the color perception test results of the second element of the image for color perception test displayed in the first display step and the second element of the image for color perception test in the second display step are different.

According to the invention according to claim 8, it is possible to reduce influences of color stimulation of the last image for color perception test (that is, to reduce the influences of color adaptation to the last image for color perception test) and to execute more accurate color perception test since the image in gray color is displayed when switching the images for color perception test.

PREFERRED EMBODIMENT

Figure 1:
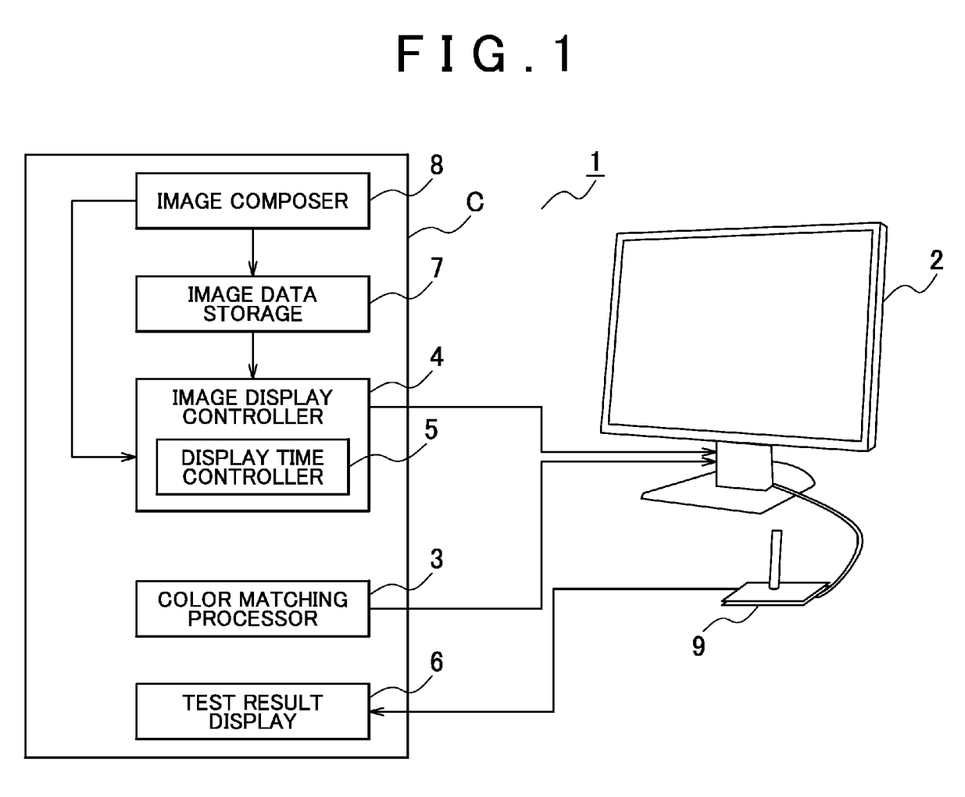
FIG. 1 is block diagram that shows an instance of a structure of a color perception tester according to the invention.
Figure 2:
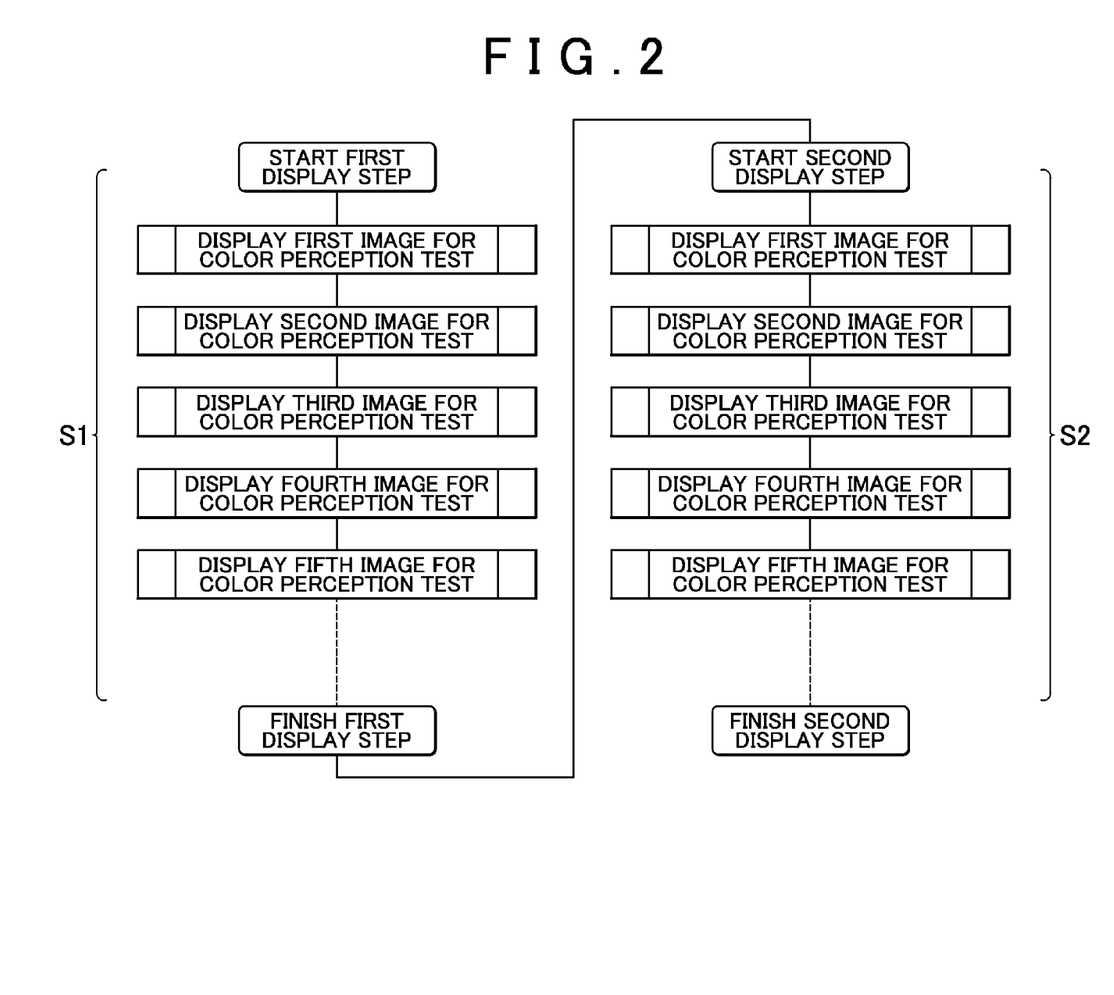
FIG. 2 is a flowchart that shows an instance of a method of displaying an image for color perception test.
Figure 3:
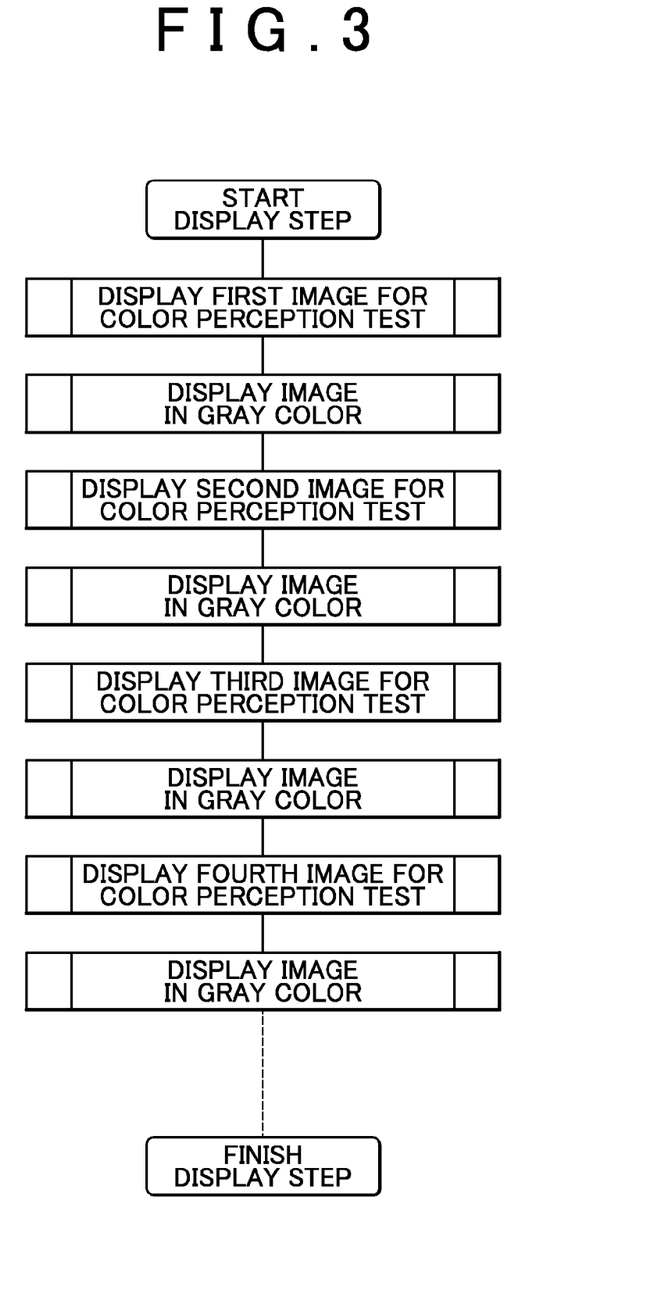
FIG. 3 is a flowchart that shows the other instance of the method of displaying the image for color perception test.

An embodiment of the invention is now explained, referring to appended drawings FIGS. 1 to 3.

A color perception tester according to the invention is a device for displaying two or more images for a color perception test on a color monitor in order, switching these images. Such images for color perception test are images as shown in ISHIHARA Color vision test and images each showing some stimulus, such as characters, numbers and Landolt rings, in a background, for instance. And, the color monitors are liquid crystal monitors, for instance, but may be the other type of monitors, well known monitors, such as CRTs and plasma displays. Preferably, entry of outside light into such a monitor is blocked since the monitor may receive outside light, such as sunshine and room light and the color of the image may receive an influence of the outside light and change. Preferably, shading hood on the market that is dedicated for the color monitor, such as "CH2", "CH3" and "CH4 made by NANAO CORPORATION may be used, or the color monitor may be located into some shading case for shading outside light so that an examinee can watch the color monitor through an observation hole.

A color perception tester according to the invention denoted with a reference number 1 has a color matching processor 3 that does a color matching processing on a color monitor 2 on a color monitor 2 and an image display controller 4 that executes at least one display step wherein two or more images for color perception test are displayed on the color monitor 2 on which the color matching processing was done in order. When displaying two or more images for color perception test in the one display step, the image display controller 4 changes one element ("the first element" in the specification) of six elements, hue of each image for color perception test, brightness of each image for color perception test, saturation of each image for color perception test, display time of each image for color perception test, and brightness of a background or a stimulus if the image for color perception test is comprised of the background image (in an optional color) and the stimulus shown in the background image (that is, changes the first element of each image for color perception test that is displayed in the display step), and fixes five elements excluding the first element. If the image for color perception test that is comprised of the background image and the stimulus shown in the background image is not used in the color perception test, one element (the first element) of the four elements, the hue, the brightness, the saturation and the display time of each image for the color perception test may be changed and the remaining three elements may be fixed. In the specification, the color matching processing is one for keeping the same colors so as not to change colors that the color monitor displays with passage of time. Preferably, the above-mentioned color matching processor 3 is comprised of a sensor (not shown) that detects the colors that the color monitor 2 displays so as to show with values, and a color corrector (not shown) that corrects the colors that the color monitor 2 displays by feedback control with the values from the sensor. It is ideal that such a matching processing is done before the color perception test, but it may be done after such a test since several minutes or so are taken for the processing. If the matching processing every 200 hours is recommended as a specification of the color monitor, the color matching processing may be automatically started and the power may be automatically shut down after such a processing when using time from the last matching processing exceeds 150 hours and "power off" is operated after finishing the color perception test. On the other hand, if the brightness of the image for color perception test or the brightness of the background image is changed as the first element, it is not necessary to continuously change the brightness (for instance, it is not necessary that the image to be firstly displayed is displayed in the darkest color and the images are displayed with gradually brighter colors), and the brightness may be freely changed. When the saturation or the hue of the image for color perception test is changed as the first element, it is not necessary to continuously change it and it may be freely changed, similarly. If the display time of the image for color perception test is changed as the first element, but, it is necessary that the display time of the image for color perception test that to be firstly displayed is the shortest and the display time of the images for color perception test is gradually longer.

According to the invention, it is possible to do a correct color perception test since the color matching processor 3 that does the color matching processing is provided and the image for color perception test is not changed with passage of time that is different from the image printed on a book or a card with colors and the color quality can be kept. Even if reexamination is done on some examinee after passage of several months or several years, it is possible to correctly know a degree of decreasing of a color perception function by aging since the color quality of the image for color perception test is not changed with passage of time as a color printed one.

The image display controller 4 may execute at least two display steps. That is, the image display controller 4 may execute at least two display steps, a first display step (see S1 of FIG. 2) wherein two or more images for color perception test are displayed in order on the color monitor 2 on which the color matching processing was done, and a second display step (see S2 of FIG. 2) wherein two or more images for color perception test are displayed in order on the color monitor 2. Preferably, the image display controller 4 may change the first element when displaying each image for color perception test in the respective display steps S1, S2, may change any one of the elements excluding the first element (referred to as "the second element" in the specification) in the first display step S1 ad the second display step S2 gradually (that is, the second element is fixed as a stable value in the first display step S1 and the second element is fixed as the different value in the second display step S2), and may fix four elements excluding the first and second elements during the first display step S1 and the second display step S2. If the image for color perception test that is comprised of the background image and the stimulus shown in the background image is not used in the color perception test, one (the first element) of four elements, the hue, the brightness, the saturation and the display time of each image for color perception test is changed when displaying each image for color perception test in each display step, any one excluding the first element (the second element) is changed in the first display step S1 and the second display step S2 gradually (that is, is fixed as a stable value in the first display step S1 and is fixed as a different value in the second display step S2), and two elements excluding the first element and the second element are fixed during the first display step S1 and the second display step S2. By doing so, more detailed test result can be obtained by comparing the color perception test results of the second element of the image for color perception test displayed in the first display step S1 and the second element of the image for color perception test displayed in the second display step S2 since both elements are different. FIG. 2 has two display steps, but may have three display steps without limiting to two.

In this case, a display time controller 5 that controls the display time of each image for color perception test is provided at the image display controller 4, preferably. By doing so, credibility of the test results can be improved by preventing from widely varying the display time of each image for color perception test.

Preferably, a test result display 6 is provided so as to display a result showing whether or not an examinee can perceive the image for color perception test, a kind of the displayed image for color perception test, information on combination of colors that are used in the displayed image for color perception test, and the display time of the image for color perception test. The test results displayed on the test result display 6 may be displayed on the color monitor 2, or may be printed.

Preferably, an image data storage 7 that stores two or more images for color perception test may be provided, and the image display controller 4 may display the image for color perception test stored in the image data storage 7. Furthermore, an image composer 8 that is possible to compose the image for color perception test to be displayed through examiners may be provided so that the image display controller 4 can display the image for color perception test composed by the image composer 8. Preferably, an instruction to the image composer 8 from the examinee (the instruction in connection with shapes, sizes or colors of the stimulus) may be done through switches, push buttons or a user interface (the user interface displayed on the monitor screen). Preferably, the image for color perception test composed by the image composer 8 is temporarily stored in the image data storage 7, and thereafter, is displayed through the image display controller 4.

In such a case, a response means 9, such as a joint stick and a keyboard, may be provided, so that the examinee himself (herself) inputs such a result whether the examinee perceived the image for color perception test or the examinee responds such a result in words and inputs the result through the examiner.

Preferably, the monitor may display the image in gray color during switching the image for color perception test, that is, for a predetermined time after finishing displaying an image for color perception test before starting to display the next image for color perception test through the image display controller 4, as shown in FIG. 3. By doing so, it is possible to reduce influences of color stimulation of the last image for color perception test (that is, to reduce the influences of color adaptation to the last image for color perception test) and to execute more accurate color perception test.

Preferably, the color perception tester 1 according to the invention has a statistical data computer (not shown) that computes the test results of the color perception test done on two or more examinees (referred to as "the examinee group" hereinafter) as statistical data, and an accumulated data storage that stores two or more statistical data obtained from the examinee group (the statistical data obtained from the examinee group in their twenties, the statistical data obtained from the examinee group in their thirties, the statistical data obtained from the examinee group in their forties and the like, for instance) as accumulated data, and a data comparator (not shown) that compares the test result of the color perception test done on some examinee and the accumulated data. By doing so, it is possible to compare the test result of the color perception test of some examinee and the accumulated data of the examinee group with each other and to statistically evaluate the color perception function of new examinee (in other words, relative evaluation when comparing with the examinee group).

On the other hand, a control program according to the invention is a program for controlling a computer ("C" of FIG. 1), and through which the computer C functions as the color matching processor 3 for doing the color matching processing of the color monitor 2 and the image display controller 4 for doing at least one display step wherein two or more images for color perception test are displayed in order on the color monitor 2 on which the color matching processing was done, and besides, the computer C functions such that the image display controller 4 can change any one element (the first element) of the six elements, the hue, the brightness, the saturation, the display time of each image for color perception test, and the brightness of the background or the stimulus if the image for color perception test is comprised of the background image (the background image in optional color) and the stimulus shown in the background image and fix the five elements excluding the first element when displaying two or more images for color perception test in the one display step. If the image for color perception test that is comprised of the background image and the stimulus shown in the background image is not used in the color perception test, one (the first element) of the four elements, the hue, the brightness, the saturation and the display time of each image for color perception test may be changed and the remaining three element may be fixed.

In such a case, the image display controller 4 may execute at least two display steps, the first display step S1 wherein two or more images for color perception test are displayed in order on the color monitor 2 on which the color matching processing was done, and the second display step S2 wherein two or more images for color perception test are displayed in order on the color monitor. Preferably, the image display controller 4 changes the first element when displaying each image for color perception test in the respective display steps S1, S2, and changes any one element (the second element) excluding the first element gradually in the first display step S1 and the second display step S2 (that is, the second element is fixed as a predetermined value in the first display step S1 and the second element is fixed as a different value in the second display step S2), and the four elements excluding the first element and the second element are fixed during the first display step S1 and the second display step S2. If the image for color perception test that is comprised of the background image and the stimulus shown in the background image is not used in the color perception test, preferably one (the first element) of the four elements, the hue, the brightness, the saturation and the display time of each image for color perception test is changed when displaying each image for color perception test in each step, one element (the second element) excluding the first element is gradually changed in the first display step S1 and the second display step S2 (that is, is fixed as a predetermined value in the first display step S1 and is fixed as a different value in the second display step S2), and two elements excluding the first element and the second element are fixed during the first display step S1 and the second display step S2.

Preferably, the above-mentioned program may function as the statistical data computer that computes the test result of the color perception test done on the examinee group as the statistical data, the accumulated data storage that stores two or more statistical data obtained from the examinee group as the accumulated data and data comparator that compares the test result of the color perception test done on some examinee and the accumulated data. By doing so, it is possible to obtain relative evaluation on the new examinee in comparison with the examinee group.

Preferably, a method of controlling the color perception tester according to the invention has a step of executing the color matching processing on the color monitor 2 through the color matching processor 3 and a step of executing at least one display step wherein two or more images for color perception test are displayed in order on the color monitor 2 on which the color matching processing was done through the image display controller 4, characterized in that the image display controller 4 changes one element (the first element) of six elements, the hue, the brightness, the saturation and the display time of each image for color perception test and the brightness of the background or the stimulus if the image for color perception test is comprised of the background image (the background in an optional color) and the stimulus shown in the background image, and the fixes five elements excluding the first element when displaying two or more images for color perception test in the one display step. If the image for color perception test that is comprised of the background image and the stimulus shown in the background image is not used in the color perception test, one (the first element) of the four elements, the hue, the brightness, the saturation and the display time of each image for color perception test may be changed and the remaining three elements may be fixed.

Preferably, in such a case, the image display controller executes at least two display steps, the first display step S1 wherein two or more images for color perception test are displayed in order on the color monitor on which the color matching processing was done, and the second display step S2 wherein two or more images for color perception test are displayed in order on the color monitor, and the image display controller changes the first element when displaying each image for color perception test in each display step, and changes one element (the second element) excluding the first element gradually in the first display step S1 and the second display step S2, and fixes the four elements excluding the first element and the second element during the first display step S1 and the second display step S2. If the image for color perception test that is comprised of the background image and the stimulus shown in the background image is not used in the color perception test, one (the first element) of the four elements, the hue, the brightness, the saturation and the display time of each image for color perception test is changed when displaying each image for color perception test in each display step, and one element (the second element) excluding the first element is gradually changed in the first display step S1 and the second display step S2 (that is, is fixed as a predetermined value in the display step S1, and is fixed as a different value in the second display step S2), and two elements excluding the first element and the second element are fixed during the first display step S1 and the second display step S2.

The above-mentioned steps may have a step wherein the statistical data computer computes the test result of the color perception test done on the examinee group as the statistical data, a step wherein the accumulated data storage stores two or more statistical data obtained from the examinee group as the accumulated data, and a step wherein the data comparator compares the test result done on some examinee with the accumulated data. By doing so, it is possible to obtain relative evaluation on the new examinee in comparison with the examinee group.

EXPLANATION OF REFERENCE NUMBERS

1 . . . color perception tester
2 . . . color monitor
3 . . . color matching processor
4 . . . image display controller
5 . . . display time controller
6 . . . test result display
7 . . . image data storage
8 . . . image composer
C . . . computer
S1 . . . first display step
S2 . . . second display step

The invention claimed is:

1. A color perception tester, comprising:
a color matching processor that executes a color matching processing on a color monitor;
an image display controller that executes at least one display step wherein two or more images for color perception test are displayed in order on said color monitor on which said color matching processing was done;
whereby said image display controller changes display time of each image for color perception test so as to become gradually longer as a first element, or changes one element of five elements, of: a hue, a brightness, a saturation of each image for color perception test, and a brightness of a background image in an optional color or a stimulus if said images for color perception test are comprised of said background image and said stimulus shown in said background image as said first element in such a state that said display time is fixed when displaying said two or more images for color perception test in said one display step
wherein said image display controller executes at least two display steps, a first display step wherein two or more images for color perception test are displayed in order on said color monitor on which said color matching processing was done, and a second display step wherein two or more images for color perception test are displayed in order on said color monitor, and said image display controller changes said first element when displaying each image for color perception test in each display step, and changes a second element, excluding said first element of six elements of: hue, brightness, saturation and display time of each image for color perception test and brightness of a background image in an optional color or a stimulus if said images for color perception test are comprised of said background image and said stimulus shown in said background image gradually in said first display step and said second display step and fixes four elements excluding said first element and said second element during said first display step and said second display step.

2. The color perception tester according to claim 1 wherein said image display controller has a display time controller that controls display time of each image for color perception test.

3. The color perception tester according to claim 1 of further comprising a test result display that displays an image for color perception test, information on color combination used in displayed image for color perception test, a result whether or not an examinee can perceive said displayed image for color perception test and display time of said displayed image for color perception test.

4. The color perception tester according to claim 1 further comprising an image data storage that stores two or more images for color perception test, wherein said image display controller displays said images for color perception test stored in said image data storage.

5. The color perception tester according to claim 1 further comprising an image composer that composes said images for color perception test to be displayed, wherein said images display controller displays said image for color perception test that were composed through said image composer.

6. The color perception tester according to claim 5, further comprising an image data storage that stores two or more images for color perception test, wherein said images for color perception test composed through said image composer are temporally stored in said image data storage.

7. The color perception tester according to claim 1 wherein said image display controller displays an image in gray color on said color monitor for a predetermined time during switching said images for color perception test.

8. The color perception tester according to claim 1 further comprising a statistical data computer that computes test results of a color perception test done on two or more examinees, comprising an examinee group, as statistical data, an accumulated data storage that stores two or more statistical data obtained from said examinee group as accumulated data, and a data comparator that compares a test result of said color perception test done on at least one of said examinees with said accumulated data.

9. The color perception tester according to claim 1 wherein said images for color perception test includes figures comprising characters, numerals, and Landolt rings, in a background image.

10. The color perception tester according to claim 1 wherein a user is capable of selecting to change display time of said images for color perception test as said first element, to change hue of said images for color perception test as said first element, to change brightness of said images for color perception test as said first element, to change saturation of said images for color perception test as said first element, or to change brightness of said background image or said stimulus as said first element.

11. The color perception tester according to claim 1, whereby said image display controller changes a brightness of said background image in an optional color or said stimulus if said images for color perception test are comprised of said background image and said stimulus shown in said background image as said first element in such a state that said display time is fixed when displaying said two or more images for color perception test in said one display step.

12. A method for controlling a color perception tester, by providing a computer to function as at least one member of the group comprising, a color matching processor that executes a color matching processing on a color monitor; and an image display controller that executes at least one display step wherein two or more images for color perception test are displayed in order on said color monitor on which said color matching processing was done; whereby said image display controller changes display time of each image for color perception test so as to become gradually longer as a first element, or changes one element of five elements, of: a hue, a brightness, a saturation of each image for color perception test, and a brightness of a background image in an optional color or a stimulus if said images for color perception test are comprised of said background image and said stimulus shown in said background image as the first element in such a state that said display time is fixed when displaying said two or more images for color perception test in said one display step and wherein said image display controller executes at least two display steps, a first step wherein two or more images for color perception test are displayed in order on said color monitor on which said color matching processing was done, and a second display step wherein two or more images for color perception test are displayed in order on said color monitor; and said image display controller changes said first element when displaying each image for color perception test in each display step, and gradually changes said second element that is excluding said first element of six elements a hue, a brightness, a saturation, a display time of each image for color perception test, and a brightness of a background image in an optional color or a stimulus if said images for color perception test are comprised of said background image and said stimulus shown in said background image in said first display step and said second display step, and fixes four elements excluding said first element and said second element in said first display step and said second display step.

13. The method according to claim 12, for providing said computer to function as at least one member of the group comprising:
a statistical data computer that computes test result of a color perception test done on two or more examinees comprising an examinee group, as statistical data,
an accumulated data storage that stores two or more statistical data obtained from an examinee group as accumulated data; and
a data comparator that computes said test result of said color perception test done on at least one examinee with said accumulated data.

14. The method according to claim 12 wherein said images for color perception test include figures comprising characters, numerals and Landolt rings, in a background image.

15. The method according to claim 12 wherein a user is capable of selecting to change display time of said images for color perception test as said first element, to change hue of said images for color perception test as said first element, to change brightness of said images for color perception test as said first element, to change saturation of said images for color perception test as said first element, or to change brightness of said background image or said stimulus as said first element.

16. The method according to claim 12, whereby said image display controller changes a brightness of said background image in an optional color or said stimulus if said images for color perception test are comprised of said background image and said stimulus shown in said background image as said first element in such a state that said display time is fixed when displaying said two or more images for color perception test in said one display step.

17. The method of controlling a color perception tester comprising:
 a step of executing a color matching processing on a color monitor through a color matching processor;
 a step of executing at least one display step wherein two or more images for color perception test are displayed in order on said color monitor on which said color matching processing was done through an image display controller;
 whereby said image display controller changes display time of each image for color perception test so as to become gradually longer as a first element, or changes one element of five elements of: a hue, a brightness, a saturation of each image for color perception test, and a brightness of a background image in an optional color or a stimulus if said images for color perception test are comprised of said background image and said stimulus showing in said background image as the first element in such a state that said display time is fixed when displaying said two or more images for color perception test in said one display step
 wherein said image display controller executes at least two display steps, a first display step wherein two or more images for color perception test are displayed in order on said color monitor on which said color matching processing was done, and a second display step wherein two or more images for color perception test are displayed in order on said color monitor, and said image display controller changes said first element when displaying each image for color perception test in each display step, and changes a second element, excluding said first element of six elements of: a hue, a brightness, a saturation and a display time of each image for color perception test and a brightness of a background image in an optional color or a stimulus if said images for color perception test are comprised of said background image and said stimulus shown in said background image gradually in said first display step and said second display step and fixes four elements excluding said first element and said second element during said first display step and said second display step.

18. The method of controlling the color perception tester according to claim 17, further comprising:
 a step of computing test result of a color perception test done on two or more examinees comprising an examinee group as statistical data through a statistical data computer, a step of storing two or more statistical data obtained from said examinee group as accumulated data through an accumulated data storage; and a step of comparing a test result of said color perception test done on at least one examinee with said accumulated data through a data comparator.

19. The method of controlling the color perception tester according to claim 17 wherein said images for color perception test include figures, comprising characters, numerals and Landolt rings, in a background image.

20. The method of controlling the color perception tester according to claim 17 wherein a user is capable of selecting to change display time of said images for color perception test as said first element, to change hue of said images for color perception test as said first element, to change brightness of said image for color perception test as said first element, to change saturation of said images for color perception test as said first element, or to change brightness of said background image or said stimulus as said first element.

21. The method of controlling color perception tester according to claim 17 whereby said image display controller changes a brightness of said background image in an optional color or said stimulus if said images for color perception test are comprised of said background image and said stimulus shown in said background image as said first element in such a state that said display time is fixed when displaying said two or more images for color perception test in said one display step.

* * * * *